United States Patent [19]

Sederholm

[11] Patent Number: 5,782,929
[45] Date of Patent: Jul. 21, 1998

[54] ACETABULAR SHELL HAVING SINTERED SCREW HOLE PLUGS

[75] Inventor: Gary W. Sederholm, Austin, Tex.

[73] Assignee: Sulzer Orthopedics Inc., Austin, Tex.

[21] Appl. No.: 777,268

[22] Filed: Dec. 31, 1996

[51] Int. Cl.[6] ................................ A61F 2/32
[52] U.S. Cl. .................................... 623/22
[58] Field of Search .................. 623/16, 18, 19, 623/20, 22, 23, 66

[56] References Cited

U.S. PATENT DOCUMENTS

| | | |
|---|---|---|
| 5,137,535 | 8/1992 | Keller ........................ 623/23 |
| 5,314,487 | 5/1994 | Schryver et al. ............. 623/22 |
| 5,360,452 | 11/1994 | Engelhardt et al. ......... 623/22 |
| 5,370,702 | 12/1994 | Jones ......................... 623/22 |
| 5,571,198 | 11/1996 | Drucker et al. ............. 623/22 |
| 5,645,606 | 7/1997 | Oehy et al. ................. 623/22 |

*Primary Examiner*—David Isabella
*Attorney, Agent, or Firm*—Kenneth S. Barrow

[57] ABSTRACT

An acetabular shell can receive bone screws through a screw hole that is initially occluded by a plug in sintered connection with the wall of the screw hole. The sintered connection can be broken to permit removal of the plug, if desired. The plug prevents migration of wear debris from the interior of the shell to the exterior of the shell through an unused screw hole.

15 Claims, 1 Drawing Sheet

ACETABULAR SHELL HAVING SINTERED SCREW HOLE PLUGS

BACKGROUND OF THE INVENTION

1. Field of the Invention

The present invention relates generally to implantable prostheses for human joint replacement, and relates more particularly to an acetabular cup for a hip prosthesis.

2. Background Information

A total hip prostheses includes a femoral component and an acetabular cup component. The femoral component has a stem for receipt and fixation within the femoral canal at a resected proximal end of the femur and has a spherical head that may be integral with or removably attached to the stem. The acetabular cup has an outer surface for receipt within a reamed acetabulum and has an inner bearing cavity for receiving the head of the femoral component. The head articulates relative to the bearing cavity such that the total hip prosthesis restores motion to a diseased or damaged hip joint.

One known general configuration for an acetabular cup involves an outer acetabular shell made of a biocompatible metal such as titanium, and a bearing insert made of a biocompatible plastic such as ultra-high molecular weight polyethylene. The acetabular shell has a generally hemispherical cup shape, defined by a generally spherical outer surface and a generally spherical inner surface with a shell wall between the inner and outer surfaces. The inner wall defines a generally hemispherical shell cavity having an opening for receipt of the bearing insert. The bearing insert has a generally spherical outer surface dimensioned to be received and fixed within the shell cavity of the acetabular shell, and has a bearing cavity facing outwardly for receipt of the head of the femoral component.

Acetabular shells of such known construction can be affixed to the bone of the patient's acetabulum by bone screws or bone cement. If bone screws are selected, the screws are inserted through screw holes in the acetabular shell prior to insertion of the bearing insert into the shell. The shell can also be affixed by a combination of bone screws and bone cement. The acetabular shell can be provided with a plurality of screw holes in excess of the number of bone screws that typically would be used by the implanting physician, to provide a selection of screw sites. Thus, some of the provided screw holes may be used while others are left open, or, in the case where no bone screws are used, all of the screw holes are left open.

Although the bearing insert is usually designed to be received in non-articulating relationship within the acetabular shell, it is believed that a small amount of relative motion between the bearing insert and the acetabular shell nevertheless occurs under the varying load that the acetabular cup is subjected to during use. Such small relative motion, or micro-motion, may result in wear at the interface between the bearing insert and acetabular shell, resulting in the generation of polyethylene or metal debris. It has been suggested that such debris can migrate out of the acetabular cup and come in contact with bone, possibly resulting in osteolysis, which ultimately can lead to bone resorption and possible loosening of the acetabular prosthesis. One apparent pathway for the migration of debris out of the acetabular shell is through open screw holes.

It would be desirable to provide an acetabular shell, designed for use with a bearing insert, that is provided with screw holes for receipt of bone screws, wherein unused screw holes would be occluded to prevent migration through such unused screw holes of wear debris generated within the acetabular shell. This and other desirable features are provided by the present invention.

SUMMARY OF THE INVENTION

An acetabular shell is provide that can receive bone screws, if desired. Screw holes are provided in the wall of the acetabular shell. The screw holes extend through the wall of the acetabular shell and are open at both ends. In the shell as delivered to the surgeon, each screw hole is initially occluded by a separate plug that is sintered to the wall of the screw hole. The plug can be removed by the surgeon pre-operatively, if desired, to permit a bone screw to be received through the screw hole. If desired, the plug can be left in place if the screw hole is not to be used to receive a bone screw, thereby preventing migration of wear debris from the interior of the acetabular shell to the exterior of the shell through an open, unused screw hole.

In accordance with one aspect of the invention, there is provided a generally hemispherical cup-shaped shell having an inner surface and an outer surface defining a shell wall therebetween. The shell wall has at least one screw hole therethrough defined by a screw hole wall extending from the inner surface to the outer surface of the shell. Disposed within the screw hole is a plug having a perimetrical edge, said perimetrical edge being connected in sintered attachment to said screw hole wall to occlude said screw hole.

It is an object of the present invention to provide an acetabular shell that presents the physician with the choice of using bone screws or not to secure the shell in the acetabulum, while providing for occlusion of any screw holes that are not selected to receive a bone screw so that migration of wear debris from the interior of the shell to the exterior through open, unused screw holes is prevented.

Other objects and advantages of the present invention will be apparent from the following descriptions of a preferred embodiment with reference to the drawings.

DESCRIPTION OF THE PREFERRED EMBODIMENT

Figure 1:
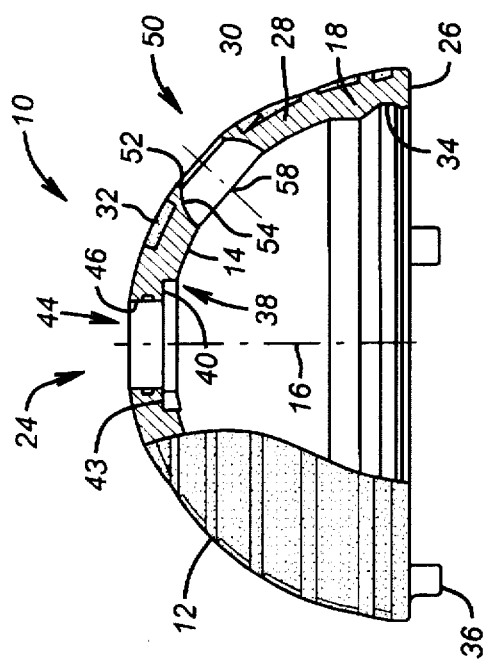
FIG. 1 is a side view of an acetabular shell constructed in accordance with the present invention, shown partially in section.
Figure 2:
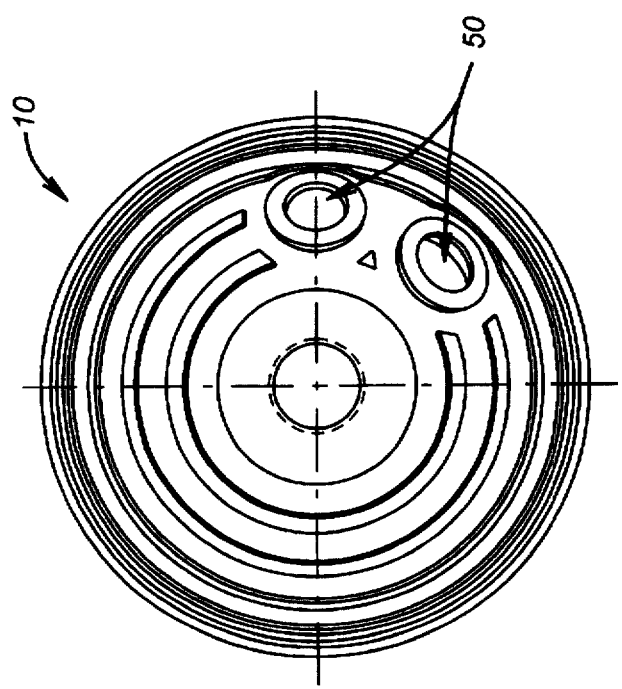
FIG. 2 is an axial view of the acetabular shell of FIG. 1 looking onto the dome of the acetabular shell.

Referring in particular to FIGS. 1 and 2, there is illustrated an acetabular shell 10 generally shaped as a hemispherical cup defined by an outer hemispherical surface 12 and an inner hemispherical surface 14 having centers that lie on a common axis 16. Inner and outer surfaces 12 and 14 define therebetween a shell wall 18 having an apex 24 and an annular rim 26.

Shell wall 18, preferably constructed of solid titanium metal or titanium alloy, has areas of reduced thickness 28 due to recesses 30 in the outer surface 12. Recesses 30 are filled with a porous titanium coating 32 to a level substantially flush with outer surface 12. The porous coating 32 provides a surface that promotes adhesion of bone cement to acetabular shell 10 and that is capable of promoting and accepting ingrowth of bone therein in non-cemented applications.

An annular groove 34 is located in inner surface 14 proximate rim 26 for the purpose of receiving a corresponding elastically deformable annular protrusion on the outer surface of a polyethylene bearing insert (not shown). Annular groove 34 in cooperation with the annular protrusion of the polyethylene bearing insert serves to axially retain the bearing insert within acetabular shell 10.

A plurality of legs 36 are circumferentially spaced about rim 26 and extend axially therefrom for receipt within radial notches in a flange (not shown) of the polyethylene bearing insert. Receipt of the legs 36 within the said notches retains the bearing insert against rotation about axis 16.

A recess 38 having a flat end wall 40 and a side wall 42 made assymetrical by notch 43 is located in inner surface 14. Recess 38 serves to receive a positioning tool for holding and positioning acetabular shell 10 within the acetabulum during implantation.

A dome hole 44 is centered at the apex 24 in coaxial alignment with axis 16. Dome hole 44 is bounded by a substantially cylindrical side wall 46 extending from outer hemispherical surface 12 to flat end wall 40 of recess 38. Side wall 46 of dome hole 44 is threaded to receive a threaded plug (not shown) inserted from the cavity side of shell 10. The threaded plug is inserted after shell 10 has been positioned within the acetabulum and the positioning tool has been removed from engagement with recess 38 and dome hole 44, for the purpose of occluding dome hole 44 to prevent debris migration therethrough.

Figure 3:
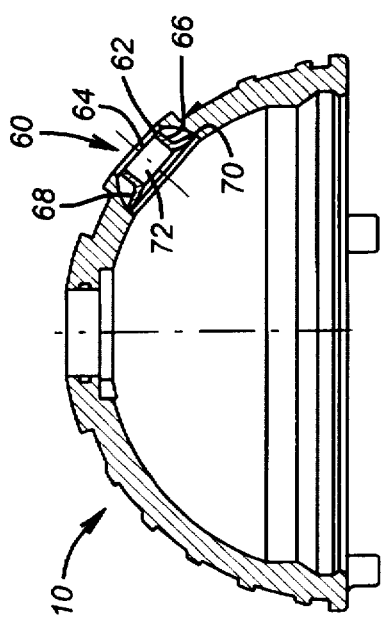
FIG. 3 is an enlarged cross-section of a portion of the shell wall of the acetabular shell of FIG. 1, showing a section through a screw hole, and further including a screw hole plug in sintered attachment to the screw hole wall.

Referring in particular to FIGS. 1 and 3, screw hole 50 is described. In the embodiment illustrated herein, there are preferably two screw holes 50 provided in addition to dome hole 44, as is evident in FIG. 2. It should nevertheless be understood that the present invention is also useful in connection with any number of screw holes that may be distributed across acetabular shell 10 to provide the implanting surgeon with a selection of sites for inserting a bone screw, with the understanding that not all of the screw holes so provided would necessarily be used during any particular implantation. Screw hole 50 is bounded by a substantially cylindrical side wall 52 extending from outer hemispherical surface 12, and a spherical surface 54 extending from said side wall 52 to the inner hemispherical surface 14. Surface 54 is concave toward the interior of acetabular shell 10 and has its center 58 located radially inwardly of inner surface 14. Surface 54 as shown is spherically configured for the purpose of engaging a spherical undersurface of the head of a bone screw. Alternatively, surface 54 could be conically configured for engaging a screw having a head with a conical undersurface. Screw hole 50 extends through shell wall 18 and is open at both ends.

Figure 4:
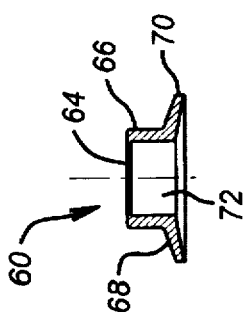
FIG. 4 is an enlarged cross-sectional view of the screw hole plug of FIG. 3.

With particular reference to FIGS. 3 and 4, screw hole plug 60 includes a cylindrical portion 62 defined by an end wall 64, and a cylindrical side wall 66. A frustoconical flange portion 68 extends from cylindrical side wall 66 radially outwardly and axially away from cylindrical portion 62. Flange portion 68 terminates in a perimetrical edge 70, of approximately 0.020 inches thickness. Cylindrical portion 62 includes a blind hole 72 therein that is open at that end from which flange portion 68 extends, i.e., blind hole 72 is open toward the cavity of shell 10.

Plug 60 is constructed of titanium metal or titanium alloy. Plug 60 is preferably of the same composition as shell wall 18, but is manufactured separately from shell wall 18. After screw hole 50, and any other similar screw holes, have been machined in shell wall 18, plug 60 is inserted within screw hole 50 with a force just sufficient to press flange edge 70 against screw hole wall 54 such that plug 60 is retained within screw hole 50 in a weak press-fit relationship. Subsequently, shell 10, with porous coating 32 and screw plugs 60 in place, is sintered in an oven for several hours at about 2200 degrees Farenheit, resulting in point-contact metalurgical adhesion of the particles of the porous coating to each other and to shell wall 18, and of perimetrical edge 70 of plug 60 to screw hole wall 54 of screw hole 50. The resulting sintered connection between plug 60 and screw hole wall 54 is sufficient to prevent plug 60 from being inadvertently dislodged during normal handling and implantation of shell 10, but is also weak enough to permit plug 60 to be readily removed by the implanting surgeon, if desired. Removal of plug 60 is accomplished by use of an elongate tool having a cylindrical tip configured to fit closely within blind hole 72. By inserting the tip of the elongate tool within blind hole 72 and using the length of the tool to apply leverage, the sintered connection between flange edge 70 and screw hole wall 54 can be easily broken, whereby plug 60 can be removed to leave screw hole 50 unoccluded for receipt of a bone screw therethrough.

While a particular preferred embodiment of the present invention has been described, it should be appreciated that other configurations of the screw hole and perimetrical edge of the plug that provide the same result of a sintered connection that is sufficiently strong to allow the plug to occlude the screw hole against migration of debris therethrough, while being sufficiently weak to be readily broken with intent, will be apparent to those of ordinary skill in the art.

In addition, the sintered plug arrangement as described herein can be used in connection with any hole in an acetabular shell where it is desired to provide the choice of occluding or opening the hole, regardless of the intended purpose of the hole.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

I claim:

1. An acetabular shell that can be used with or without bone screws, comprising:

a generally cup-shaped metal shell having an inner surface and an outer surface defining a shell wall therebetween, said shell wall having at least one hole wall defining a hole extending from said inner surface to said outer surface, said hole being occluded by a metal plug having a perimetrical edge, said perimetrical edge being in sintered connection with said screw hole wall.

2. A method of making an acetabular shell that can be used with or without bone screws, comprising the steps of:

a) providing a generally cup-shaped metal shell having an inner surface and an outer surface defining a shell wall therebetween;

b) creating a hole through said shell wall extending from said inner surface to said outer surface and having a hole wall;

c) providing a plug having a perimeter;

d) inserting said plug into said hole such that said perimeter is in contact with said hole wall; and e) heating said shell and plug to create a sintered metallurgical connection between said plug perimeter and said hole wall.

3. The acetabular shell of claim 1, in which said hole wall includes a surface portion that is concave toward the interior of the acetabular shell.

4. The acetabular shell of claim 3, in which said concave surface portion of said hole wall is spherically curved.

5. The acetabular shell of claim 4, in which said concave, spherically curved surface portion of said hole wall has a center of curvature located radially inwardly of the inner surface of the shell.

6. The acetabular shell of claim 1, in which said plug includes a flange portion, said perimetrical edge being located on said flange portion.

7. The acetabular shell of claim 6, in which said plug includes a cylindrical portion from which said flange portion extends radially outwardly.

8. The acetabular shell of claim 7, in which said flange portion of said plug is frustoconical.

9. The acetabular shell of claim 6, in which said perimetrical edge has a thickness of about 0.020 inches.

10. The acetabular shell of claim 7, in which said cylindrical portion of said plug includes a blind hole therein for receiving a tool to facilitate removal of said plug from said hole.

11. The method of claim 2, in which said step of providing a plug includes providing said plug having a flange portion, said perimeter of said plug being located on said flange portion.

12. The method of claim 11, in which said step of providing a plug includes providing said plug having a cylindrical portion from which said flange portion extends radially outwardly.

13. The method of claim 12, in which said step of providing a plug includes providing said plug having a flange portion that is frustoconical.

14. The method of claim 11, in which said step of providing a plug includes providing said plug having a perimetrical edge having a thickness of about 0.020 inches.

15. The acetabular shell of claim 12, in which said step of providing a plug includes providing said plug having a blind hole in said cylindrical portion of said plug for receiving a tool to facilitate removal of said plug from said hole.

* * * * *